United States Patent [19]

Wakasugi et al.

[11] Patent Number: 5,495,050

[45] Date of Patent: Feb. 27, 1996

[54] DEPOLYMERIZATION OF CHLOROALDEHYDE CYCLIC TRIMERS

[75] Inventors: Takashi Wakasugi; Tadashi Miyakawa; Fukuichi Suzuki, all of Iwaki, Japan

[73] Assignee: Kureha Chemical Industry Co., Ltd., Tokyo, Japan

[21] Appl. No.: 326,272

[22] Filed: Oct. 20, 1994

[30] Foreign Application Priority Data

Dec. 17, 1993 [JP] Japan .................. 5-344328

[51] Int. Cl.$^6$ .................. C07C 45/55; C07C 47/14
[52] U.S. Cl. .................. 568/483; 569/457
[58] Field of Search .................. 568/483, 457

[56] References Cited

U.S. PATENT DOCUMENTS

| | | | |
|---|---|---|---|
| 2,714,616 | 8/1955 | Schnizer et al. | 560/457 |
| 2,722,552 | 11/1955 | Zellner et al. | 260/601 |
| 3,183,270 | 5/1965 | Evers et al. | 568/457 |
| 3,801,645 | 4/1974 | Dalman . | |

FOREIGN PATENT DOCUMENTS

| | | | |
|---|---|---|---|
| 5202026 | 10/1993 | Japan . | |
| 929034 | 6/1963 | United Kingdom | 568/483 |

OTHER PUBLICATIONS

Plewe et al., "(+)-Erythro-Gamma, Delta-Dihydroxycarboxylic Acid Lactones From a Beta-Lithiopropionate Equivalent and Alpha-Chloroaldehydes", *Synthesis-Stuttgart*, 7:534–536 (1989).

Takashi Wakasugi et al., "Preparation of Chloroacetaldehyde Cyclic Trimer and Its Depolymerization", *Chemistry Letters*, pp. 171–172 (1992).

Takashi Wakasugi et al., "One–pot Preparation of 2–Chloromethyldioxolanes and 2–Aminothiazoles from Chloromethyltrioxanes" *Chemistry Letters* pp. 2039–2042 (1994).

*Primary Examiner*—Joseph E. Evans
*Attorney, Agent, or Firm*—Testa, Hurwitz & Thibeault

[57] ABSTRACT

A method for producing high purity chloroaldehyde monomers at a high yield by depolymerization of a chloroaldehyde cyclic trimer represented by the following formula,

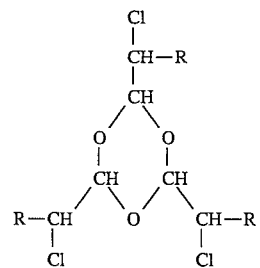

wherein R is a hydrogen atom, methyl group, or an ethyl group. The depolymerization reaction can be carried out in the presence of activated clay. Said chloroaldehyde cyclic trimer can be stored in a stable manner and chloroaldehyde monomers obtained by the depolymerization can be used as are as a raw material for the synthetic reaction of chloroaldehyde derivatives.

5 Claims, No Drawings

DEPOLYMERIZATION OF CHLOROALDEHYDE CYCLIC TRIMERS

BACKGROUND OF THE INVENTION

1. Field of the Invention

The present invention relates to an improved method for depolymerization of cyclic trimers of aliphatic aldehydes with the chlorinated 2-position (hereinafter referred to as chloroaldehyde) which is useful as a raw material for synthesis of organic chemicals.

2. Description of the Background Art

Chloroaldehydes having the chlorinated 2-position, such as monochloroacetaldehyde (hereinafter referred to as MCA) and 2-chloropropionaldehyde (hereinafter referred to as CPA), are useful compounds as raw materials for the synthesis of drugs, agricultural chemicals, and polymers. Because these are extremely unstable compounds, MCA is sold as an aqueous solution with a concentration of approximately 40% and CPA is not commercially available. Japanese Patent Laid-open (Kokai) Nos. 223575/1990 and 173785/1992 therefore propose to store these chloroaldehydes in a stable manner as cyclic trimers and obtain MCA or CPA by depolymerizing the trimers upon use.

The method disclosed by these Japanese Patent Laid-open specifications comprises depolymerizing the chloroaldehyde cyclic trimers using a catalyst such as p-toluenesulfonic acid or sulfuric acid at 120°–130° C. in the absence of a solvent. However, the depolymerization of these trimers using p-toluenesulfonic acid or sulfuric acid as a catalyst in the absence of a solvent involves various side reactions of monomers produced, causing production of high boiling point components. Because of this, it is essential to separate the products by distillation after the depolymerization reaction. Carbonated residues obtained by the distillation must be appropriately treated and washed, which makes it difficult for the catalyst to be recycled for reuse.

SUMMARY OF THE INVENTION

In view of this situation, the present invention has an object of providing a method for the depolymerization of chloroaldehyde cyclic trimers, such as MCA trimer and CPA trimer, in which a. distillation is not required to remove the catalyst used.

This object of the present invention can be achieved by a method for the depolymerization of a chloroaldehyde cyclic trimer represented by the following formula,

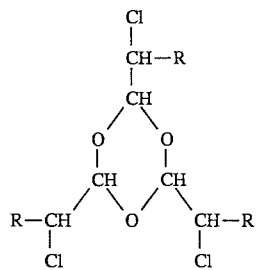

wherein R is a hydrogen atom, a methyl group, or an ethyl group, characterized by carrying out said depolymerization reaction in the presence of activated clay.

In the present invention a chloroaldehyde cyclic trimer is depolymerized in the presence of activated clay in the absence or presence of a solvent.

According to the present invention chloroaldehyde monomers which can be used as are for the synthesis of chloroaldehyde derivatives can be supplied by the depolymerization of chloroaldehyde cyclic trimers.

Other and further objects, features and advantages of the present invention will appear more fully from the following description.

DETAILED DESCRIPTION OF THE INVENTION AND PREFERRED EMBODIMENTS

In the present invention activated clay is used as a catalyst for the depolymerization of chloroaldehyde cyclic trimers. Examples of the activated clay which can be used include Girdler-K series activated clays, such as Girdler K10 (trademark, Nissan Girdler Catalyst Co., Ltd.), Fuller's earth, and the like. The amount of the catalyst used is 1–20%, preferably 2–18%, for the amount of the chloroaldehyde cyclic trimers. Either powdery or spherical activated clay can be used.

The depolymerization can be achieved without using a solvent at a high yield involving production of very little by-products by using activated clay as a catalyst.

In the depolymerization of chloroaldehyde cyclic trimers in the absence of a solvent, monomers can be reproduced by refulxing at 70°–130° C. for 5 minutes to 2 hours. The liquid reaction product thus obtained comprise chloroaldehyde monomers and a small amount of raw material trimers. In most cases, activated clay does not inhibit succeeding synthetic reactions, and the depolymerization reaction products can be subject to the synthetic reaction of chloroaldehyde derivatives without removing the catalyst. The catalyst, however, may be recovered by filtration prior to or after the synthetic reaction of chloroaldehyde derivatives, and the recovered catalyst may be recycled for reuse.

The depolymerization can be carried out also in the presence of an organic solvent. Aromatic compounds such as toluene and benzene, aliphatic cyclic compounds such as cyclohexane, and aliphatic compounds such as heptane can be used as the solvent. The reaction temperature is below the refluxing temperature of the solvent used, preferably at 60°–130° C. The depolymerization reaction of chloroaldehyde cyclic trimers can be carried out by reacting for 30 minutes to 3 hours using said catalyst and said solvent. The chloroaldehyde in an organic solvent thus obtained can be stored in a stable manner at room temperature and can be used as a raw material for the synthesis of chloroaldehyde derivatives without removing the catalyst. The catalyst may be removed by filtration prior to or after the synthetic reaction and the recovered catalyst can be recycled for reuse.

According to the method of the present invention the chloroaldehyde cyclic trimers can be depolymerized either in an organic solvent or in the absence of a solvent. A high purity chloroaldehyde monomer can be obtained at a high yield without a distillation procedure, so that the production steps are simplified. Furthermore, because the catalyst can be reclaimed by a simple filtration procedure and recycled for reuse, the depolymerization reaction is adaptable to an industrial scale depolymerization reaction of chloroaldehyde cyclic trimers.

Other features of the invention will become apparent in the following description of the exemplary embodiment which is given for illustration of the invention and is not intended to be limiting thereof. In the examples below, a depolymerization yield refers to the proportion of chloroaldehyde monomers for the trimers used in the reaction.

EXAMPLE

Example 1

(Solvent-free depolymerization reaction of MCA trimer)

5 g (21.23 mmol) of MCA trimer and 0.30 g (6% of the trimer) of Girdler K10 (trademark, Nissan Girdler Catalyst Co., Ltd.) were charged in a 50 ml three-necked flask equipped with a reflux condenser and reacted at 110° C. After 30 minutes, the composition of the reaction product was analyzed by gas chromatography to confirm production of MCA monomer. The depolymerization yield was 95%. No peaks other than those for MCA and MCA trimer were found in the chromatogram.

6 g (96.77 mmol) of ethylene glycol was charged to the depolymerization reaction solution, and the mixture was reacted at 80° C. for 2 hours. The reaction product was distilled to obtain 7.0 g (57.14 mmol) of 2-chloromethyl-1,3-dioxolane. The yield based on the trimer initially charged was 90%.

Example 2

(Solvent-free depolymerization reaction of CPA trimer)

5 g (18.02 mmol) of CPA trimer and 0.25 g (5% of the trimer) of Girdler K10 (trademark, Nissan Girdler Catalyst Co., Ltd.) were charged in a 50 ml three-necked flask equipped with a reflux condenser and reacted at 110° C. After 30 minutes, the composition of the reaction product was analyzed by gas chromatography to confirm production of CPA monomer. The depolymerization yield was 95%. No peaks other than those for CPA and CPA trimer were found in the chromatogram.

5 g (80.65 mmol) of ethylene glycol was charged to the depolymerization reaction solution, and the mixture was reacted at 80° C. for 2 hours. The reaction product was distilled to obtain 6.50 g (47.62 mmol) of 2-(1-chloroethyl)-1,3-dioxolane. The yield based on the trimer initially charged was 88%.

Example 3–8

(Depolymerization reaction of MCA trimer in an organic solvent)

5 g of MCA trimer was dissolved in 30 ml of the solvent shown in Table 1. The solution was charged in a 0 ml three-necked flask equipped with a reflux condenser and the depolymerization reaction was carried out for 2 hours under the conditions shown in Table 1.

The catalysts, the reaction conditions, and depolymerization yields based on the trimer initially charged were shown in Table 1, in which the amount of the catalyst refers to the proportion of the catalyst for the initially charged MCA trimer and the depolymerization yields were measured by gas chromatography analysis.

The Fuller's earth recovered from the reaction product of Example 4 by filtration was used in Example 5.

The Girdler K10 recovered from the reaction product of Example 7 by filtration was used in Example 8.

TABLE 1

| Example | Catalyst | Amount of Catalyst (%) | Solvent | Reaction temp. (°C.) | Depolymerization yield (%) |
|---|---|---|---|---|---|
| 3 | Fuller's earth | 3 | toluene | 110 | 96 |
| 4 | Fuller's earth | 5 | toluene | 110 | 97 |
| 5 | Fuller's earth | 5 | toluene | 110 | 90 |
| 6 | Fuller's earth | 5 | benzene | 70 | 70 |
| 7 | Girdler K10 | 5 | toluene | 110 | 92 |
| 8 | Girdler K10 | 5 | toluene | 110 | 87 |

Example 9

(Depolymerization reaction of CPA trimer in an organic solvent )

5 g of CPA trimer, 0.25 g (5% of the trimer) of Girdler K10 (trademark, Nissan Girdler Catalyst Co., Ltd.), and 30 ml of toluene were charged in a 50 ml three-necked flask equipped with a reflux condenser and the depolymerization reaction was carried out at 110° C. for 2 hours. After the reaction, the composition of the reaction product was analyzed by gas chromatography to confirm production of CPA monomer. The depolymerization yield was 93%.

Comparative Example 1

(Solvent-free depolymerization reaction of MCA trimer)

5 g of MCA trimer and 0.30 g (6% of the trimer) of p-toluenesulfonic acid were charged in a 50 ml threenecked flask equipped with a reflux condenser and reacted at 110° C. After 30 minutes, the composition of the reaction product was analyzed by gas chromatography to confirm production of MCA monomer and a number of high boiling point products. The depolymerization yield was 56%.

Comparative Example 2

(Depolymerization of MCA trimer by distillation)

10 g of MCA trimer and 0.5 g of p-toluenesulfonic acid were charged in a 50 ml three-necked flask equipped with a reflux condenser and distilled under atmospheric pressure at 115° C. 9.2 g of the distillate thus obtained was analyzed by gas chromatography to confirm production of MCA monomer. The depolymerization yield was 92%.

Carbonated products were confirmed in the flask bottom residue. 10 g of MCA trimer was added to this residue and atmospheric distillation was carried out. The depolymerization yield was 54%.

Obviously, numerous modifications and variations of the present invention are possible in light of the above teachings. It is therefore to be understood that within the scope of the appended claims, the invention may be practiced other than as specifically described herein.

What is claimed is:

1. A method for depolymerization of a chloroaldehyde cyclic trimer represented by the following formula,

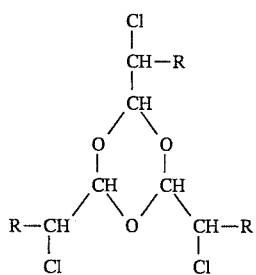

wherein R is a hydrogen atom, methyl group, or an ethyl group, characterized by carrying out the depolymerization reaction in the presence of activated clay.

2. The method according to claim 1, wherein the activated clay is used in an amount of 1–20% for the amount of the chloroaldehyde cyclic trimer.

3. The method according to claims 1 or 2, wherein the depolymerization of chloroaldehyde cyclic trimers is carried out at 70°–130° C. without using a solvent.

4. The method according to claims 1 or 2, wherein the depolymerization of chloroaldehyde cyclic trimers is carried out at 60°–130° C. in the presence of a solvent.

5. The method according to claims 1 or 2, wherein said clay is a Girdler-K series clay or Fuller's earth.

* * * * *